United States Patent
Eberhart et al.

(10) Patent No.: US 7,048,696 B2
(45) Date of Patent: *May 23, 2006

(54) GUIDE-WIRE MOUNTED BALLOON MODULATION DEVICE AND METHODS OF USE

(75) Inventors: Mark Eberhart, Glenmoore, PA (US); William T. Fisher, Schwenksville, PA (US); John E. Nash, Chester Springs, PA (US); Dennis M. Sauro, Glenmoore, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/144,088

(22) Filed: Jun. 2, 2005

(65) Prior Publication Data

US 2005/0228314 A1    Oct. 13, 2005

Related U.S. Application Data

(63) Continuation of application No. 10/227,996, filed on Aug. 26, 2002, now Pat. No. 6,902,535.

(51) Int. Cl.
*A61B 5/00* (2006.01)
*A61M 25/00* (2006.01)
*A61M 29/00* (2006.01)

(52) U.S. Cl. ............... 600/585; 604/96.01; 604/99.01; 604/104; 606/191

(58) Field of Classification Search ........ 600/433–435, 600/585; 604/96.01, 98.01, 97.01–97.03, 604/99.01–99.04, 101.01, 104, 264, 523, 604/98, 97, 99, 10; 606/191–200

See application file for complete search history.

(56) References Cited

U.S. PATENT DOCUMENTS

| | | |
|---|---|---|
| 3,477,438 A | 11/1969 | Allen et al. |
| 3,495,594 A | 2/1970 | Swanson |
| 3,837,381 A | 9/1974 | Arroyo |
| 4,332,254 A | 6/1982 | Lundquist |
| 4,653,539 A | 3/1987 | Bell |
| 4,654,027 A | 3/1987 | Dragan et al. |
| 4,752,287 A | 6/1988 | Kurtz et al. |
| 4,759,751 A | 7/1988 | Gabel et al. |
| 4,790,813 A | 12/1988 | Kensey |
| 4,911,163 A | 3/1990 | Fina |
| 5,749,371 A | 5/1998 | Zadini et al. |

(Continued)

FOREIGN PATENT DOCUMENTS

WO    WO 97/27896    8/1997

(Continued)

*Primary Examiner*—Charles Marmor
(74) *Attorney, Agent, or Firm*—Jeffrey R. Ramberg

(57) ABSTRACT

An apparatus for modulating the pressure of a fluid such as a gas within the expandable portion of a guide wire catheter. A preferred embodiment apparatus features a means for controllably gripping and releasing the open, proximal end of a tubular guide wire, means for introducing a fluid to a desired pressure and volume into the expandable portion of the tubular guide wire through the open end, and, while maintaining the pressure and volume of fluid in the tubular guide wire, a means for introducing a sealing member into the open end of said tubular guide wire to seal the fluid in the tubular guide wire. In a particularly preferred embodiment, the apparatus also features a deflation tool for piercing the seal and letting the fluid out. Using this apparatus, the tubular guide wire can be re-sealed and re-opened as necessary.

17 Claims, 3 Drawing Sheets

U.S. PATENT DOCUMENTS

| | | |
|---|---|---|
| 5,807,330 A | 9/1998 | Teitelbaum |
| 6,176,844 B1 | 1/2001 | Lee |
| 6,179,815 B1 | 1/2001 | Foote |
| 6,234,996 B1 | 5/2001 | Bagaoisan et al. |
| 6,251,084 B1 | 6/2001 | Coelho |
| 6,325,778 B1 | 12/2001 | Zadno-Azizi et al. |
| 6,348,048 B1 | 2/2002 | Andrea et al. |
| 6,431,039 B1 | 8/2002 | Jacobsen et al. |
| 6,475,185 B1 | 11/2002 | Rauker et al. |
| 6,902,535 B1 * | 6/2005 | Eberhart et al. ............ 600/585 |
| 6,932,828 B1 * | 8/2005 | Bonnette et al. ............ 606/194 |
| 6,942,678 B1 * | 9/2005 | Bonnette et al. ............ 606/191 |
| 2001/0016704 A1 | 8/2001 | Zadno-Azizi et al. |
| 2003/0088194 A1 | 5/2003 | Bonnette et al. |
| 2003/0088262 A1 | 5/2003 | Bonnette et al. |
| 2003/0088263 A1 | 5/2003 | Bonnette et al. |

FOREIGN PATENT DOCUMENTS

| | | |
|---|---|---|
| WO | WO99/42161 | 8/1999 |

\* cited by examiner

GUIDE-WIRE MOUNTED BALLOON MODULATION DEVICE AND METHODS OF USE

BACKGROUND OF THE INVENTION

This is a Continuation of U.S. patent application Ser. No. 10/227,996, filed on Aug. 26, 2002 in the names of Mark Eberhart et al., now U.S. Pat. No. 6,902,535, and entitled "GUIDE-WIRE MOUNTED BALLOON MODULATION DEVICE AND METHODS OF USE". The entire contents of this commonly owned patent application are expressly incorporated herein by reference.

The use of a balloon attached to the end of a guide-wire is not new, see for example U.S. Pat. No. 6,251,084 (Coelho), and U.S. Pat. No. 4,790,813 (Kensey). In this arrangement, the guide-wire is actually a small diameter tube, with the lumen therethrough serving to allow fluid to be injected, and with the fluid being an agent used to expand the balloon.

The balloon may serve various functions (e.g., locating and/or securing the wire or associated device within the artery, securing a wire within a catheter, or blocking the distal flow of fluid and/or debris created during one or more of the procedures).

The balloon/guide-wire system may be used in various types of therapeutic and/or diagnostic procedures (e.g., percutaneous transluminal angioplasty, stent placement, the placement of ultrasonic or other diagnostic instruments, and the placement of thrombectomy devices, etc.). During the procedure several catheters or elongate instruments (together "catheters") may be used sequentially, with the same guide-wire. Inserting instruments over, or alongside, a single guide-wire saves procedural time, since only one guide-wire would need to be placed. This approach may also improve safety, and reduce chance of infection, etc.

Inserting a plurality of catheters, whether singularly or concurrently, requires the catheter(s) to be placed over the proximal end of the guide-wire. Where the guide-wire is arranged with a balloon at or near the distal end, the catheter(s) would need to be passed over any valve located at the proximal end of the guide-wire.

Multiple catheters are commonly used when, for example, a physician performs an angiogram or other diagnostic procedure, and then decides to perform angioplasty or other therapeutic procedure or other interventional procedure. Most interventional procedures will require the placement of a guide wire for the subsequent delivery of the interventional instruments, and more recently some guide wires incorporate distal balloons to protect the distal tissues from debris generated during those same procedures. Since treatment and diagnostic procedures are becoming more commonplace, and the advancements in each of these technologies have led to procedures using even more catheters. These catheters are continually getting smaller, which allows the physician to reach tighter arteries and lumens within the body.

For distal protection to be effective the balloon must remain inflated as catheters are exchanged over the guide wire. This necessitates a small diameter valve, which some refer to as a low-profile valve. Self-sealing valves have previously been disclosed; see for example U.S. Pat. No. 3,477,438 (Allen, et al.), U.S. Pat. No. 3,495,594 (Swanson), U.S. Pat. No. 3,837,381 (Arroyo), and U.S. Pat. No. 4,752,287 (Kurtz, et al.). These valves are commonly made from elastic (Allen, et al., and Kurtz, et al.) or resilient (Swanson) materials, and may require pressure in the system to operate (Arroyo). The properties of these valve materials, together with their operational pressures, require various of these valves to have large sealing areas. This does not facilitate the design of smaller catheters. Additionally, the valves would ideally operate over a wide range of pressures; including positive and negative pressures.

Check valves have also been disclosed, see for example U.S. Pat. No. 4,653,539 (Bell), however these are directional valves, and therefore will not operate in both positive and negative pressure environments. Employing a vacuum in the system during navigation will facilitate the securing of the balloon to the guide-wire, that is, the balloon will stay folded or otherwise securely pressed against the side of the wire. This may allow the system to navigate tighter vessels or lumens. However, check valves, such as the one disclosed by Bell, do not meet this bi-directional operation need. Additionally, this type of valve, as well as the previously described self-sealing valves, require a syringe or special instrument to allow evacuation around the valve's sealing surface. These syringes or needles must be in-place during the entire evacuation procedure, or the valve will cease the fluid flow. This opens the systems up to situations where malfunctions or equipment breakage may yield an inserted and expanded balloon, which may not readily be collapsed. A system is needed that will allow evacuation without the application of vacuum or other specialized components.

In addition to these stated concerns, the length of time required to complete the procedure is affected by these valves. This procedure time is of concern because of escalating medical costs, as well as the stress on the patient. These valves must allow rapid infusion and evacuation of balloon-filling fluids.

Yet another low profile catheter valve, designed to fit small diameter catheters to navigate small pathways within the body such as blood vessels and ducts, is disclosed in U.S. Pat. No. 4,911,163 (Fina). A syringe is attached to the proximal end of an elongated tubular conduit (e.g. catheter) and used to inflate a distal balloon. Once the balloon is inflated, the catheter is clamped at the proximal end, the syringe is removed, and a plug is inserted into the lumen of the catheter, and then the clamp is removed. The plug is retracted and reinserted to adjust the balloon inflation volume as needed, using this same multi-step procedure. Needless to say, this type of valve is tedious to handle and the need for a separate clamping system further complicates the procedure and may potentially damage the catheter. Certainly the clamping pressures are very high, in order to totally collapse the circular catheter bore such that fluid will not leak (until the plug is inserted). Reinflating the balloon would also cause integrity problems if the catheter were reclamped at the same location.

Another such low profile catheter valve is disclosed in U.S. Pat. No. 6,325,778 (Zadno-Azizi, et al.). This valve features a needle which is inserted coaxially with the guidewire, wherein the needle is arranged to cover a fluid outlet port. The rate of balloon inflation and collapse is limited by the rate at which gas leaves the fluid outlet port. Since the fluid outlet port is radially outward from the guidewire's longitudinal axis, its size is geometrically constrained; that is, the larger diameter of the port, the less strength the guide-wire has. Since the guide-wire must withstand significant bending and torsional stress during the procedure, the port must be significantly less than the inside diameter of the guide-wire, thereby limiting the rate of evacuation of the balloon-filling fluid.

This slow evacuation phenomenon may have been recognized by Coelho, as the disclosure prescribes a vacuum to collapse the balloon. Indeed, the tortuous path in the orifice of the Coelho device, through which the balloon inflation fluid is evacuated, must be nearly as small as the one disclosed by Zadno-Azizi. Here, the orifice must be considerably smaller than the inside diameter of the guide-wire, because the path of fluid escape is through a self-sealing valve; and the valve must have sufficient integrity to cause a seal against itself, after an evacuation needle is withdrawn.

A valve which may utilize the overall inside diameter (or bore) of the guide wire is disclosed in U.S. Pat. No. 5,807,330 (Teitelbaum). The two basic concepts disclosed by Teitelbaum are a valve that is basically an insert with threads, wherein the threads secure the valve in the proximal end of the guide-wire; and an insert with a press-fit geometry, that is pressed into the proximal end of the guide-wire. Both of these concepts suffer similar shortcomings.

The threaded insert requires extremely fine threads, which are expensive and tedious to manufacture even before considering the limited wall thickness of the guide-wire available for threading (perhaps only a few thousandths of an inch). Additionally, it is extremely difficult to align small threaded parts of this sort, which leads to misalignment and cross-threading. This problem would be especially prevalent where the same valve was actuated more than once during the same procedure—a common occurrence.

The press-fit geometry requires parts of very tight tolerance, which are also tedious and expensive to produce. Press-fit components are normally manufactured for mechanical support, but press-fitting to cause a gas impermeable seal is possible; however, the insert would require an extremely uniform surface, which mates exactly with the inside surface at the proximal end of the guide-wire. It is this guide-wire surface which poses great manufacturing challenges.

Boring or machining the inside surface of the guide-wire is very challenging because of the fine wall thickness—perhaps only a few thousandths of an inch. Machining of this component may produce irregular wall thinning, since no tube inside and outside is truly concentric, which could lead to premature failure.

The aforementioned threaded and press-fit concepts disclosed by Teitelbaum both suffer manufacturing challenges as well as economic disadvantages. Finally, they have features that may lead to premature failure, necessitating removal of the device, following by re-insertion of a new balloon/guide-wire assembly.

It is the intent of the embodiments of the present invention to overcome these and other shortcomings of the prior art.

SUMMARY OF THE INVENTION

These and other objects of this invention are achieved by providing a valve mechanism for inflating and deflating a balloon or other expandable member on a guide-wire or catheter (e.g., at or near the distal end of a guide-wire), such that while the balloon is inflated, the proximal end of the wire would have a low profile and would not interfere with the use of other interventional devices using over-the-wire technique or rapid exchange systems. The system basically consists of detachable tools, one each for inflation and deflation of the balloon; additionally the inflation tool features in a preferred embodiment a gripping means, an inflating means, and a sealing means.

The inflation tool serves the functions of gripping and releasing the guide wire proximal end; providing a means of modulating the pressure inside the guide wire resulting in balloon or expandable member inflation; and applying a deformable plug into the bore of the guide wire.

In use, the proximal end of the guide wire is inserted into a chamber of the inflation tool; pressure is introduced via the inflation means thereby inflating the balloon or expandable member. The detachable inflation tool inserts a malleable plug in the proximal bore of the guide wire, thereby avoiding the need for costly machining and stringently tight tolerances of other devices, in order to maintain pressure within the guide wire upon the detaching the inflation tool. The sealing means prevents the escape of fluid (e.g., gas or liquid) from the guide wire for the duration of the procedure, or until release of pressure becomes necessary.

The deflation tool serves the function of relieving the pressure in the balloon or expandable member of the guide wire, by piercing the sealing means in the proximal bore of the guide wire, and upon tool removal allows the fluid contained therein to escape. The valve mechanism herein described allows repeated inflation and deflation of the catheter or guide wire, by engaging the appropriate inflation or deflation tool.

DETAILED DESCRIPTION OF PREFERRED EMBODIMENTS

Description of Inflation Tool

Figure 1:
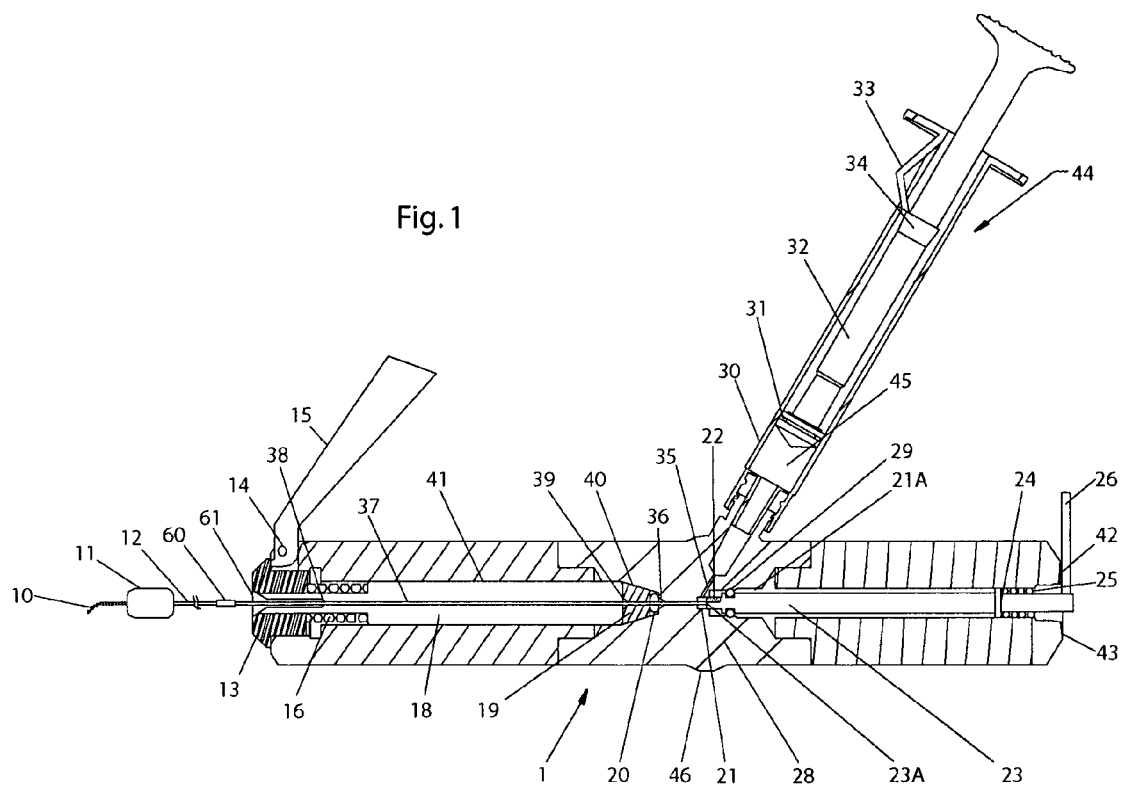
FIG. 1 is a sectional view of one design of tool for applying the sealing plug.
Figure 2:
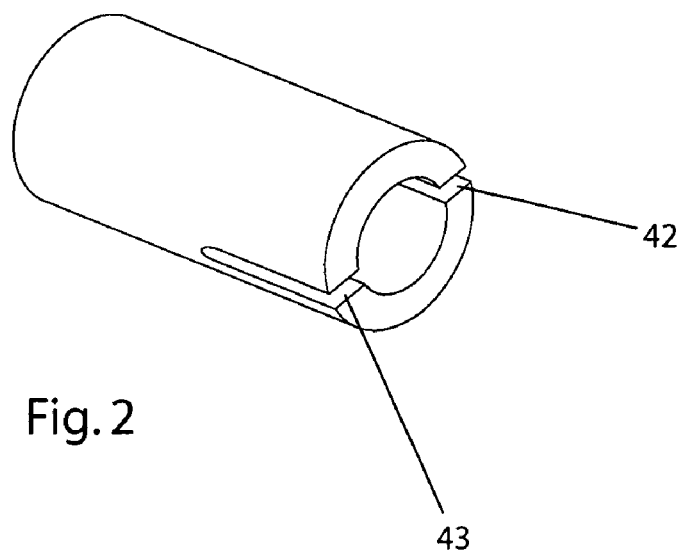
FIG. 2 is a perspective view of the cam sleeve.
Figure 3:
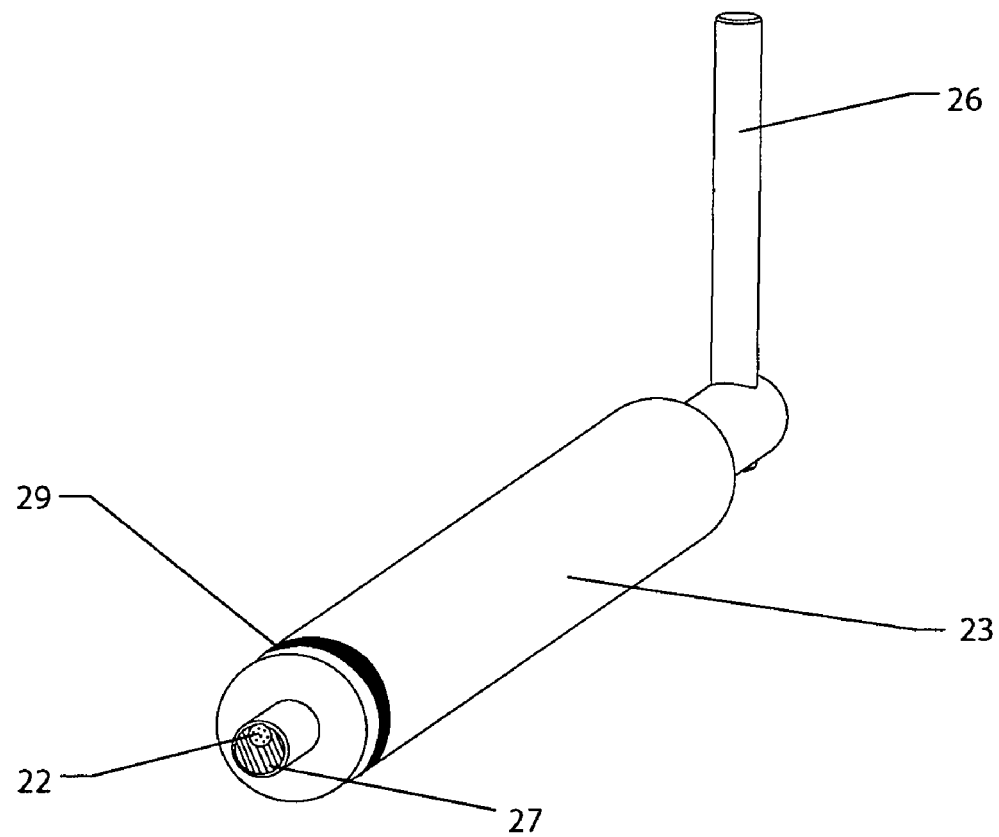
FIG. 3 is a perspective view of the sealing plug holding rod.

The preferred embodiment tool shown in FIGS. 1, 2 and 3, performs various functions, including but not limited to:

a) Gripping and releasing the guide wire proximal end;

b) Inflating the balloon on the distal end of the guide-wire, or placed somewhere therealong; and c) Applying a sealing member in the proximal bore of the guide wire.

These various device embodiments comprise sealing means, gripping means, and inflation means; while a separate device features deflation means. It is recognized that the device arranged for deflation may be attached to the device arranged for inflation (for convenience), although they may not share any componentry other than structural or housing. Additionally, it is contemplated by this invention that an inflation device or "inflation tool" may not necessarily comprise each of a gripping means, an inflation means, and a sealing means. As a non-limiting example, it is recognized that the inflation means may be a traditional syringe (where the inflation device was arranged to accept same). It is also recognized that the gripping means may be useful to perform other functions (e.g., gripping tubes at diagnostic and/or therapeutic equipment inlet ports, e.g., those found on bypass and dialysis machines.)

Referring now to FIGS. 1, 2, and 3, describing a preferred embodiment of the inflation tool, wherein like numbers indicate like components. A preferred gripping means is disclosed, wherein a tubular guide wire 12, enters bore 37 in shaft 18 and passes through deformable member 19, through pierceable diaphragm 20, into cavity 21, and stops against the face 23A of rod 23. Shaft 18 is slidably mounted in bore 41 of housing 28, and, driven proximally (relative to the guide-wire 12) by spring 16, thereby compressing deformable member 19 against the tapered bore 40 in housing 28. Pierceable diaphragm 20 is an intact disc until pierced by the entering tubular guide wire 12, the purpose of the diaphragm being to capture a charge of fluid (e.g., $CO_2$ or saline) in cavities 45, 21, and channel 35, prior to the piercing by the guide-wire 12. Axial compression of the deformable member 19 results in the tubular guide wire 12 being gripped as the deformable member is moved radially inward by the taper 40. An alternative to the pierceable diaphragm for retaining the charge of fluid in the cavity 21 and 45 is to ship the assembly with a smooth mandrel gripped in the deformable member 19 (not shown).

In a preferred embodiment, the gripping means further features an insertion-release means, wherein the shaft 18 can be driven distally (relative to the guide-wire 12) by movement of lever 15 which, pivoting on pin 14, moves the cone 13 attached to shaft 18. Thus movement of the lever 15 radially inward relieves the pressure on the deformable member 19 and hence releases the guide wire 12 (the same feature may also be used in reverse, to assist the entry of the guide-wire into the device, as will be described later).

In a preferred embodiment the inflation tool features a sealing means, with the sealing means arranged to deliver a sealing member material into the guide-wire to effect a seal, as will be described later. In this embodiment, the sealing means is preferentially located at the proximal end of the device, wherein there exists a mounted rod 23 which can move axially and rotationally in bore 21A of housing 28. Rod 23 is driven distally by spring 25 acting through flange 24 and is restrained by arm 26 coming in contact with one of the grooves 42 or 43. An O-ring seal 29 seals rod 23 against bore 21A. A sealing member material 22 is inserted in an off center bore in rod 23. Surface 23A of rod 23 is striated with grooves 27 to permit flow of fluid into the bore of tubular guide wire 12.

In a preferred embodiment the sealing member material is made from a plastically deformable or inelastic material, wherein such material may comprise organic and/or inorganic material. It is recognized that various materials may be suitable for this application, and the totality of material properties (e.g., strength, ductility, thixotropy, toughness, malleability, hysteresis, adhesiveness and fluid permeability, etc.) may reveal several good candidates.

In a preferred embodiment the inflation tool features inflation means. At the lower portion of FIG. 1 is shown a preferred embodiment of the inflation means, comprising an inflation syringe 44, wherein the syringe contains a barrel 30 arranged to be attached to body 28 using adhesive or a threaded joint (not shown). The charge of fluid is precharged into cavities 45, 21 and 35. A piston 31 attached to a plunger 32 drives fluid (gas or liquid) from chamber 45 via channel 35 into chamber 21 and thence into tubular guide wire 12. Another preferred embodiment additionally features a latch 33 fastened to barrel 30, wherein the latch 33 engages flange 34 after the plunger has been moved inward to deliver the fluid. The latch serves to prevent the piston and plunger from being driven back by the pressure trapped in cavity 21 (etc.) and balloon 11.

Description of Inflation Tool Use

A preferred embodiment inflation tool includes the gripping, inflation, and sealing means in combination, and allows the operator to hold the assembly 1 in one hand and with the thumb and fore-finger to squeeze the lever 15 toward the body 28 thus moving shaft 18 distally and relieving pressure on the deformable member 19. The guide wire 12 is then inserted into shaft 18, centralized by the tapered inlet 38, passed through the deformable member 19, to pierce the diaphragm 20 and come to rest against rod 23 at surface 23A. Chamfers at 39 and 36 further aid in centralizing the guide wire. Surface 23A of rod 23 is striated with fine grooves 27 to permit flow of fluid into the bore of tubular guide wire 12. When the guide wire has bottomed on surface 23A, the user releases the lever 15, whereupon the shaft 18 is propelled to proximally and deformable member 19 is placed in compression. In turn this action, through taper 40, causes the deformable member 19 to grip the guide wire 12 securely.

In a preferred embodiment, the position of the guide wire may be confirmed visually by viewing the location via the lens 46 built in to a clear plastic housing 28. Alternatively, if the housing is made from an opaque material the viewing lens 46 can be inserted in a tunnel as a separate component (not shown).

In yet another embodiment, the correct position of the guide wire 12 can alternatively be ascertained by observing the location of a contrasting band of color 60, formed on the guide wire 12, relative to the entrance 61 of shaft 18.

Now returning to the preferred combination embodiment, the plunger 32 and attached piston 31 are then driven inward to propel the fluid in cavity 45 through channel 35 into cavity 21 and thence through the bore of guide wire 12 into the balloon 11. In the case where gas is used to inflate the balloon, the plunger 32 may be driven to the bottom of the bore and allowed to return to a position controlled by flange 34 and latch 33. This over-compression of the gas permits the initial pressure to be high to overcome the balloon resistance but drops the pressure as the balloon reaches full size, thus reducing the tendency to overpressure the vessel (not shown) in which the balloon is residing.

With the balloon 11 inflated in the vessel, the arm 26 is rotated 180 degrees in this example (but any other angle would work with slots 42 & 43 placed differently) so that rod 23 revolves to place the sealing material 22 to a position opposing the guide wire 12. Then spring 25 urges rod 23 distally and drives the sealing material 22 into the open end of tubular guide wire 10 thus trapping the fluid in the guide wire and balloon. A plug 50 of sealing material 22, is driven into the bore of the tubular guide wire 12, as shown in FIG. 4.

At this point the lever 15 is again pressed inward radially and the guide wire is removed from the device, and the wire is ready for the rest of the interventional procedure, which might involve the passage of angioplasty balloons, stent balloons, diagnostic ultrasound, or other procedure requiring a balloon protected or anchored guide wire with the balloon inflated.

Description of Deflation Tool

Figure 4:
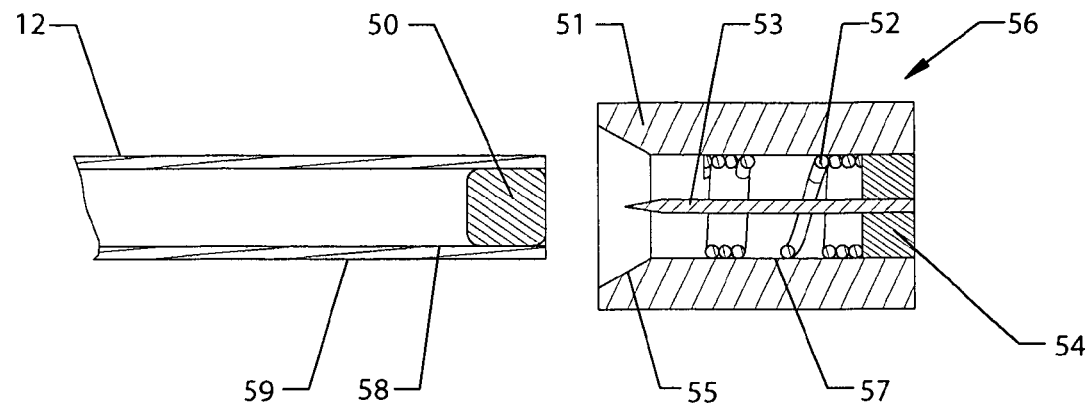
FIG. 4 is a sectional view of the deflation needle tool prior to application.
Figure 5:
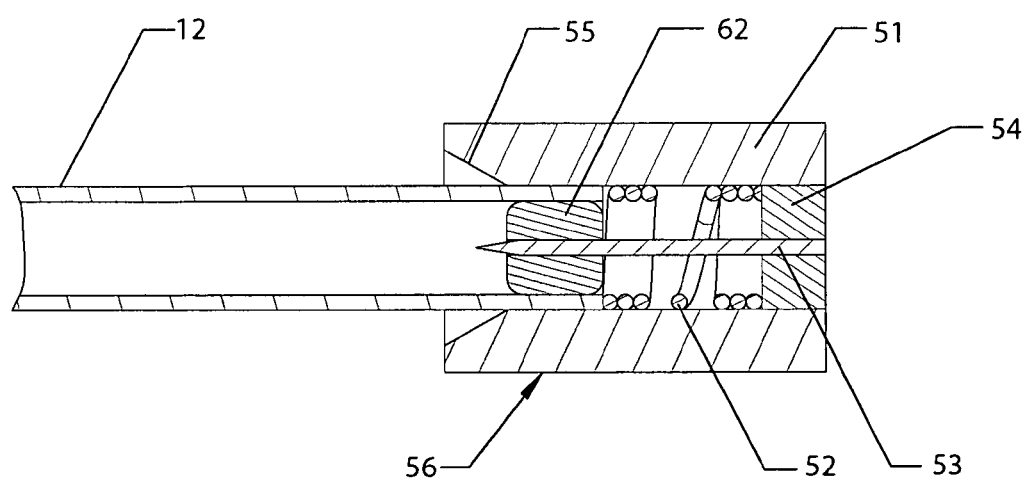
FIG. 5 is a sectional view of the deflation needle tool during application.

Referring to FIGS. 4 and 5, a preferred embodiment of the deflation tool 56 is basically constructed from four elements, a handle 51, a tube 54, a spring 52, and a needle 53. The handle has a bore 57 of about 0.016 inch diameter, a little larger than the outside diameter of the guide wire 12 which is typically 0.015 inch, and has a lead in taper 55 to allow the operator to easily locate the bore 57.

The proximal end (relative to the user's hand while utilizing the tool) of the needle 53 is held centrally in the bore 57 by tube 54. Tube 54, together with the needle 53, and the handle 51 can be assembled together by any convenient means, including but not limited to welding, using an adhesive, or a crimping operation. The needle is approximately 0.005 inch in diameter in this embodiment, and is supported by the spring coils 52 to prevent the needle from being bent during use and to align the distal end (relative to the user's hand while utilizing tool) of the needle on the centerline of the bore 57. The length of the plug 50 of sealing member material 22 (see FIG. 1) in the proximal end of the guide wire 12 is preferably about 0.030 inch long axially, although other dimensions may be more suitable depending on the composition of the sealing material and the pressure at which the balloon requires. The guide wire outside diameter 59 is typically 0.015 inch and the bore 58 can typically range from 0.011 inch to 0.005 inch. The needle needs to be sufficiently large to provide a bore through the plug 50 that it will allow the balloon to be deflated rapidly, but not so large that the plug 50 is smeared along the bore 58 too far to require a very long needle. It has been found that a 0.005 inch diameter needle permits deflation times that are acceptable (less than 30 seconds), utilizing a 0.007 inch diameter guide wire bore. Clearly these dimensions are examples only and could be adjusted to accommodate guide wires or catheters of different diameters.

The deflation tool embodiment described can be used multiple times, but it is unlikely that the operator will ever need to inflate and deflate the balloon more than 5 times in a procedure. The needle 53 is therefore preferably required to penetrate several times the length of the plug 50 into the guide wire bore 58 for this to be achieved.

Description of Deflation Tool Use

The operator inserts the proximal end of the guide wire 12 into the lead taper 55 of the deflation tool 56 compressing the spring 52 or other compressible material to the fully compressed condition. The plug 50 is pierced as shown in FIG. 5, and smears into an elongated tubular shape 62 concentric to the bore 57. The balloon 11 (see FIG. 1) then deflates due to its inherent elastic recovery, and/or vacuum can be applied to the tubular guide wire 12 by syringe or other means (neither shown) to accelerate the deflation time. The tool is then removed and is available for any subsequent use.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A valve mechanism for modulating pressure in a balloon or expandable member on or about a guide wire, the valve mechanism comprising;
    a) an inflation tool, the inflation tool comprising
        a gripping means, the gripping means comprising a deformable member and a deforming mechanism, the deforming mechanism acting upon the deformable member to cause gripping of the guide wire;
        an inflating means, the inflating means comprising a charge of fluid, and a means for modulating the pressure of the charge of fluid, and a pierceable barrier to prevent premature leakage of the charge of fluid; and
        a sealing means; the sealing means comprising a malleable material being suitable for sealing and maintaining pressure in the guide wire, and an insertion rod, the insertion rod facilitating the insertion of the malleable material into a guide wire and;
    b) a deflation tool, the deflation tool comprising a needle and a handle, the needle being adapted to penetrate and smear the malleable material into an elongated shape to allow pressure relief of the balloon or expandable member, the handle arranged to manipulate the needle.

2. The valve mechanism of claim 1, wherein said deflation tool further comprises a compressible material around said needle, with said needle being arranged within said handle, said compressible material preventing said needle from deflecting upon use.

3. The valve mechanism of claim 1, wherein said deflation tool further comprises a compressible spring around said needle, with said needle being arranged within said handle, said compressible spring preventing the needle from deflecting upon use.

4. The valve mechanism of claim 1, wherein said malleable material comprises a plastically deformable and not elastically resilient material.

5. The valve mechanism of claim 1, wherein said means for modulating the pressure of the charge of fluid comprises a syringe device.

6. The valve mechanism of claim 1, wherein said deforming mechanism comprises a lever mechanism arranged to displace a shaft proximally and distally, said shaft in turn applying and relieving pressure on said deformable member.

7. The valve mechanism of claim 1, wherein said insertion rod comprises a striated face, an off-center bore for housing said malleable material, and a lever for actuating said insertion rod.

8. The valve mechanism of claim 1, wherein said needle is suitable for repeated applications of said deflation tool, thereby allowing a plurality of cycles of inflation and deflation of said balloon or expandable member.

9. The valve mechanism of claim 1, wherein said needle is of sufficient length to allow multiple applications of said deflation tool, thereby allowing a plurality of cycles of inflation and deflation of said balloon or expandable member.

10. An apparatus for modulating the pressure of a fluid within an expandable portion of a tubular guide wire or catheter, the apparatus comprising an inflation tool comprising:
    means for controllably gripping an open, proximal end of a tubular guide wire or catheter;
    means for viewing a location of said proximal end of said tubular guide wire or catheter within said apparatus;
    means for introducing a fluid into said expandable portion of said tubular guide wire or catheter through said open, proximal end, thereby inflating said expandable portion of said tubular guide wire or catheter to a desired extent; and
    means for sealing said open proximal end of said tubular guide wire or catheter with a plastically deformable material arranged to seal said fluid in said tubular guide wire or catheter;
    said apparatus further comprising a means for re-opening said proximal end of said tubular guide wire or catheter comprising a deflation tool that comprises a needle for piercing said seal by deforming said plastically deformable material, wherein said deflation tool further comprises a handle having a bore that is open on at least one end, and wherein said needle is mounted in said bore coaxially with a centerline of said bore.

11. An apparatus for modulating the pressure of a fluid within an expandable portion of a tubular guide wire or catheter, the apparatus comprising an inflation tool comprising:
   means for controllably gripping an open proximal end of a tubular guide wire or catheter,
   means for introducing a fluid into said expandable portion of said tubular guide wire or catheter through said open end, thereby inflating said expandable portion of said tubular guide wire or catheter to a desired extent; and
   means for sealing said open proximal end of said tubular guide wire or catheter with a plastically deformable material arranged to seal said fluid in said tubular guide wire or catheter, said apparatus further comprising a means for re-opening said proximal end of said tubular guide wire or catheter comprising a deflation tool that comprises a needle for piercing said seal by deforming said plastically deformable material, wherein said deflation tool further comprises a handle having a bore that is open on at least one end, and wherein said needle is mounted in said bore coaxially with a centerline of said bore.

12. The apparatus of claim 11, further comprising a lead-in taper to said bore, and a spring held centrally in said bore to help support said needle.

13. The apparatus of claim 11, wherein said needle arranged in said bore creates a channel between said needle and an inner wall of said handle, said channel having a spring arranged therein such that said spring maintains concentricity of said needle in said bore.

14. The deflation tool of claim 11, wherein said needle is suitable for repeated applications of said deflation tool, thereby allowing a plurality of cycles of inflation and deflation of said expandable portion.

15. The needle of claim 11, wherein said needle is of sufficient length to allow multiple applications of said deflation tool, thereby allowing a plurality of cycles of inflation and deflation of said expandable portion.

16. A valve mechanism for modulating pressure in a balloon or expandable member on or about a catheter or tubular guide wire, the valve mechanism comprising:
   a) an inflation tool, the inflation tool comprising
      a gripping means, the gripping means comprising a deformable member and a deforming mechanism, the deforming mechanism acting upon the deformable member to cause gripping of the catheter or tubular guide wire;
      an inflating means, the inflating means comprising a charge of fluid, and a means of modulating the pressure of the charge of fluid, and a pierceable diaphragm to prevent premature leakage of the charge of fluid;
      a sealing means; the sealing means comprising a malleable material for sealing and maintaining pressure in the guide wire or catheter, and an insertion rod, the insertion rod facilitating the insertion of the malleable material into said catheter or tubular guide wire; and
   b) a deflation tool, the deflation tool comprising a means for penetrating and smearing the malleable material into an elongated shape to allow pressure relief of the balloon or expandable member.

17. The deflation tool of claim 16, wherein said means for penetrating and smearing the malleable material is of a length suitable for repeated applications of said deflation tool, thereby allowing a plurality of cycles of inflation and deflation of said balloon or expandable member.

* * * * *